United States Patent [19]
Freeman et al.

[11] Patent Number: 6,110,458
[45] Date of Patent: *Aug. 29, 2000

[54] CANCER THERAPY UTILIZING EX VIVO GENE TRANSDUCTION

[75] Inventors: Scott M. Freeman, New Orleans, La.; George N. Abraham, Rochester; Craig S. McCune, Huson, both of N.Y.; Frederick L. Moolten, West Newton, Mass.; David Koeplin, Los Angeles, Calif.

[73] Assignee: University of Rochester, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/450,011

[22] Filed: May 25, 1995

Related U.S. Application Data

[62] Division of application No. 08/351,891, Dec. 8, 1994, Pat. No. 5,601,818, which is a continuation of application No. 07/919,027, Jul. 23, 1992, abandoned, which is a continuation-in-part of application No. 07/736,391, Jul. 26, 1991, abandoned.

[51] Int. Cl.$^7$ ............................ A61K 48/00; C12N 15/00; C12N 15/63; C12N 5/00
[52] U.S. Cl. ................. 424/93.21; 424/93.2; 424/277.1; 435/320.1; 435/375; 435/366
[58] Field of Search ................................ 424/93.2, 93.1, 424/93.21, 277.1; 514/44; 435/320.1, 375, 366

[56] References Cited

U.S. PATENT DOCUMENTS

| | | | |
|---|---|---|---|
| 4,938,949 | 7/1990 | Borch et al. | 424/10 |
| 5,035,878 | 7/1991 | Borch et al. | 424/10 |
| 5,262,177 | 11/1993 | Brown et al. | 424/89 |
| 5,399,346 | 3/1995 | Anderson et al. | 424/93.21 |
| 5,498,410 | 3/1996 | Gleich | 424/78.36 |
| 5,580,859 | 12/1996 | Felgner et al. | 514/44 |

FOREIGN PATENT DOCUMENTS

| | | | |
|---|---|---|---|
| 93/04167 | 3/1993 | WIPO | C12N 15/00 |
| 96/21416 | 7/1996 | WIPO . | |

OTHER PUBLICATIONS

Anderson et al., Cold Spring Harbor Symp. Quant. Biol, 51, 1073 (1986).
Anderson et al., *Science*, 226, 401 (1984).
Asher et al., *J. Immunol.*, 146, 3227 (1991).
Cotter et al., *Anticancer Res.*, 10, 1153 (1990).
Drebin et al., *Cell*, 41, 695 (1985).
Eglitis et al., *Biochem. Biophys. Res. Commun.*, 151, 201 (1988).
Eglitis et al., *BioTechniques*, 6, 608 (1988).
Fearon et al., *Cell*, 60, 397 (1990).
Fialkow et al., *Biochem. Biophys. Acta*, 458, 283 (1976).
Hanahan, *Annu. Rev. Genet.*, 22, 479 (1988).
Holmes et al., *Cancer Res.*, 33, 199 (1973).
Huber, *Fed. Amer. Soc. Exper. Biol. J.*, 3, 5 (1989).
Land et al., *Science*, 222, 771 (1983).
Mann et al., *Cell*, 33, 153 (1983).
Moolton et al., *Human Gene Therapy*, 1, 125 (1990).
Moolton et al., *J. Natl. Cancer Inst.*, 82, 297 (1990).
Moolton, *Med. Hypotheses*, 24, 43 (1987).
Moolton, *Cancer Res.*, 46, 5276 (1986).
Nishiyama et al., *J. Gen. Virol.*, 45, 227 (1979).
Rosenberg et al., *New Eng. J. Med.*, 316, 889 (1987).
Russell et al., *Immunol. Today*, 11, 196 (1990).
Tsushimoto et al., *Biochem. Biophys. Acta*, 697, 14 (1982).
Wolff et al., *Science*, 247, 1465 (1990).
J. A. Eastham, et al., "Prostate Cancer Gene Therapy: Herpes Simplex Virus Thymidine Kinase Gene Transduction Followed by Ganciclovir in Mouse and Human Prostate Cancer Models", *Human Gene Therapy*, 7, 515–523, (Jan., 1996).
A. A. Elshami, et al., "Treatment of Pleural Mesothelioma in an Immunocompetent Rat Model Utilizing Adenoviral Transfer of the Herpes Simplex Virus Thymidine Kinase Gene", *Human Gene Therapy*, 7, 141–148, (Jan., 1996).
D. Klatzmann, et al., "Gene Therapy for Metastatic Malignant Melanoma: Evaluation of Tolerance to Intratumoral Injection of Cells Producing Recombinant Retroviruses Carrying the Herpes Simplex Virus Type 1 Thymidine Kinase Gene, to be Followed by Ganciclovir Administration", *Human Gene Therapy*, 7, 255–267, (Jan., 1996).
A. J. P. E. Vincent, et al., "Herpes Simplex Virus Thymidine Kinase Gene Therapy for Rat Malignant Brain Tumors", *Human Gene Therapy*, 7, 197–205, (Jan., 1996).
Acsadi, G., et al., "Direct Gene Transfer and Expression into Rat Heart in Vivo", *The New Biologist*, vol. 3, No. 1, 71–81.
Chowdhury, J.R., et al., "Long–Term Improvement of Hypercholesterolemia After ex Vivo Gene Therapy in LDL–R–Deficient Rabbits", *Science*, vol. 254, 1802–1805, (Dec. 20, 1991).
Hatzoglou, M., et al., "Hepatic Gene Transfer in Animals Using Retroviruses Containing the Promoter from the Gene for Phosphoenolpyruvate Carboxykinase", *Journal of Biological Chemistry*, 265, 17285–17293, (Oct., 1990).
Kay, M.A., et al., "Expression of human a1–antitrypsin in dogs after autologous transplantation of retroviral transduced hepatocytes", Proceeds of the National Academy of Sciences of the USA, vol. 89, No. 1, 89–93.

(List continued on next page.)

*Primary Examiner*—Karen M. Hauda
*Attorney, Agent, or Firm*—Mueting, Raasch & Gebhardt, P.A.

[57] ABSTRACT

A method is provided for eliminating cancer cells from a population of cells containing cancer cells and noncancerous cells in vitro or in vivo comprising: (a) providing a mixture of noncancerous cells and cancer cells; (b) contacting the cancer cells with transgenic cancer cells comprising a foreign gene that renders the transgenic cancer cells susceptible to a therapeutic agent; and (c) contacting the transgenic cancer cells with an amount of said therapeutic agent effective to kill both the transgenic cancer cells and the cancer cells.

17 Claims, No Drawings

OTHER PUBLICATIONS

Lin, H., et al., "Expression of Recombinant Genes in Myocardium in Vivo After Direct Injection of DNA", *Circulation*, vol. 82, No. 6, 2217–2221, (Dec., 1990).

Morgan, J.R., et al., "Expression of an Exogenous Growth Hormone Gene by Tranplantable Human Epidermal Cells", *Science*, vol. 237, 1476–1480, (Sep. 18, 1987).

Ogura, H., et al., "Implantation of Genetically Manipulated Fibroblasts into Mice as Antitumor a–Interferon Therapy", *Cancer Research*, vol. 50, 5102–5106, (Aug. 15, 1991).

Palella, T.D., et al., "Expression of human HPRT mRNA in brains of mice infected with a recombinant herpes simplex virus–1 vector", *Gene.*, vol. 80, 137–144, (1989).

Rosenberg, S.A., et al., "Gene Transfer Into Humans–Immunotherapy of Patients with Advanced Melanoma, Using Tumor Infiltrating Lymphocytes Modified by Retroviral Gene Transduction", *The New England Journal of Medicine*, 323, 570–578, (Aug., 1990).

Rosenfeld, M.A., et al., "Adenovirus–Mediated Transfer of a Recombinant a1–Antitrypsin Gene to the Lung Epithelium in Vivo", *Science*, vol. 252, 431–434, (Apr. 19, 1991).

Tani, K., et al., "Implantation of Fibroblasts Transfected with Human Granulocyte Colony–Stimulating Factor cDNA into Mice as a Model of Cytokine–Supplement Gene Therapy", *Blood*, vol. 74, No. 4, 1274–1280, (Sep. 1989).

van Beusechem, V.W., et al., "Expression of Human Adenosine Deaminase in Mice Transplanted with Hemopoietic Stem Cells Infected with Amphotropic Retroviruses", *J. Exp. Med.*, vol. 172, 729–736, (Sep., 1990).

Wilson, J.M., et al., "Temporary amelioration of hyperlipidemia in low density lipoprotein receptor–deficient rabbits transplanted with genetically modified hepatocytes", *Proc. Natl. Acad. Sci. USA*, vol. 87, 8437–8441, (Nov., 1990).

Vieweg et al (1995) Cancer Invest. 13, 193–201.

Report and Recommend. of the Panel to Assess the NIH Investment in Res. on Gene Therap., Orken et al. Dec. 1995.

Mullen (1994) Pharmac. Ther. 63, 199–207.

Gansbacher et al. (1993) Cancer Invest. 11, 345–354.

David Barba, et al., "Development of anti–tumor immunity following thymidine kinase–mediated killing of experimental brain tumors", *Proc. Natl. Acad. Sci. USA*, 91, 4348–4352, (1994).

David Barba, et al., "Thymidine kinase–mediated killing of rat brain tumors", *J. Neurosurg.*, 79, 729–735, (1993).

W. L. Bi, et al., *Hum. Gene Ther.*, 4, 725, (1993).

Bernd Bonnekoh, et al., "Inhibition of Melanoma Growth by Adenoviral–mediated HSV thymidine kinase gene transfer in vivo", *J. Invest. Derm.*, 104, 313–317, (1995).

Emiliana Borrelli, et al., "Targeting of an Inducible Toxic Phenotype in Animal Cells", *Proc. Nat'l. Acad. Sci. USA*, 85, 7572, (1988).

M. Caruso, et al., *PNAS*, 90, 7024, (1993).

S. H. Chen, et al., *Can. Res.*, 56, 3758, (1996).

S. H. Chen, et al., *PNAS*, 91, 3054, (1994).

A. Colak, et al., *Brain. Res.*, 691, 76, (1995).

Kenneth W. Culver, et al., "In Vivo Gene Transfer with Retroviral Vector–Producer Cells for Treatment of Experimental Brain Tumors", *Science*, 256, 1550–1552, (1992).

M. S. Dilber, et al., *Blood*, 88, 2192, (1995).

J. M. DiMaio, et al., *Surgery*, 116, 205, (1994).

Z. D. Ezzeddine, et al., "Selective Killing of Glioma Cells in Culture and in Vivo by Retrovirus Transfer of the Herpes Simplex Virus Thymidine Kinase Gene", *New Biol.*, 3, 608–614, (1991).

S. M. Freeman, et al., *Can. Letters*, 92, 167–174, (1995).

Scott M. Freeman, et al., "In Situ Use of Suicide Gnees for Cancer Therapy", *Seminars in Oncology*, 23, 31–45, (1996).

S. M. Freeman, et al., "The Bystander Effect: Tumor regression when a fraction of the tumor mass is genetically modified", *Cancer Res.*, 53, 5274–5284, (1993).

S. M. Freeman, et al., "The role of the immune system in the "bystander effect": new therapeutic approaches to cancer", *Lancet*, 349, 2–3, (1995).

Scott M. Freeman, et al., "Tumor Regression When a Fraction of the Tumor Mass Contains the HSV–TK Gene", Keystone Symposium on Gene Transfer, Replacement and Augmentation, Copper Mountain, Colorado, USA, Apr. 3–9, (1992).

S. Gagandeep, et al., *Can. Gene Ther.*, 3, 83, (1996).

Bernd Gansbacher, et al., "Retroviral Vector–mediated v–Interferon Gene Transfer into Tumor Cells Generates Potent and Long Lasting Antitumor Immunity", *Cancer Res.*, 50, 7820–7825, (1990).

Guenther Gastl, et al., "Retroviral Vector–mediated Lymphokine Gene Transfer into Human Renal Cancer Cells", *Cancer Res.*, 52, 6229–6236, (1992).

Paul T. Golumbek, et al., "Treatment of Established Renal Cancer by Tumor Cells Engineered to Secrete Interleukin–4", *Science*, 254, 713–716, (1991).

D. K. Hoganson, et al., *Can. Res.*, 56, 1315, (1996).

Christine E. Holt, et al., "Lipofection of cDNAs in the Embryonic Vertebrate Central Nervous System", *Neuron.*, 4, 203–214, (1990).

B. Huber, et al., *Cancer Res*, 55, 4808, (1995).

B. Huber, et al., *PNAS,*, 8302, (1994).

Brian E. Huber, et al., "Provocative Gene Therapy Strategy for the Treatment of Hepatocellular Carcinoma", *Hepatology*, 16, 273–274, (1992).

Brian E. Huber, et al., "Retroviral–mediated gene therapy for the treatment of hepatocellular carcinoma: An innovative approach for cancer therapy", *Proc. Natl. Acad. Sci. USA*, 88, 8039–8043, (1991).

Brian W. Hughes, et al., "Bystander killing of melanoma cells using the human tyrosinase promoter to express the Escherichia coli prine nucleoside phosphorylase gene", *Cancer Res.*, 55, 3339–3345, (1995).

A. Ido, et al., *Cancer Res.*, 55, 3105, (1995).

Toshiyuki Itaya, et al., "Xenogenization of a Mouse Lung Carcinoma (3LL) by Transfection with an Allogeneic Class I Major Histocompatibility Complex Gene (H–2Ld)", *Cancer Res.*, 47, 3136–3140, (1987).

M. Izquierdo, et al., *Gene Ther.*, 2, 66–69, (1995).

Shoushu Jiao, et al., "Direct Gene Transfer into Nonhuman Primate Myofibers In Vivo", *Human Gene Ther.*, 3, 21–35, (1992).

Shoushu Jiao, et al., "Persistence of Plasmid DNA and Expression in Rat Brain Cells In Vivo", *Exp. Neurol.*, 115, 400–413, (1992).

F. Kanai, et al., *Hepatology*, 23, 1359, (1996).

Yasufumi Kaneda, et al., "Increased Expression of DNA Cointroduced with Nuclear Protein in Adult Rat Liver", *Science*, 243, 375–378, (1989).

Y. Kaneko, et al., *Can. Letters*, 96, 105, (1995).

S. Kaneko, et al., *Can. Res.*, 55, 5283, (1995).

L. E. Kun, et al., *Hum. Gene Ther.*, 6, 1231–1255, (1995).

S. Kuriyama, et al., *Hepatology*, 22, 1838–1846, (1995).

Chang S. Lim, et al., "Direct In Vivo Gene Transfer into the Coronary and Peripheral Vasculatures of the Intact Dog", *Circulation*, 83, 2007–2011, (1991).

Yoshinobu Manome, et al., "Viral Vector transduction of the human deoxycytidine kinase cDNA sensitizes glioma cells to the cytotoxic effects of cytosine arabinoside in vitro and in vivo", *Nature Medicine*, 2, 567–573, (1996).

F. C. Marini, et al., *Gene Ther.*, 2, 655, (1995).

A. Maron, et al., *Gene Therp.*, 3, 315, (1996).

M. Mesnil, et al., *PNAS*, 93, 1831 (1996).

A. Dusty Miller, "Human Gene Therapy Comes of Age", *Nature*, 357, 455–460, (1992).

Frederick L. Moolten, et al., "Curability of Tumors BearingHerpes Thymidine Kinase Genes Transferred by Retroviral Vectors", *J. of the Natl Cancer Institute*, 82, 297–300, (1990).

Paula J. Mroz, et al., "Retrovirally transduced Escherichia coli gpt Genes combine selectability with chemosensitivity capable of mediating tumor eradication", *Human Gene Therapy*, 4, 589–595, (1993).

Craig A. Mullen, "Metabolic suicide genes in gene therapy", *Pharmac. Ther.*, 63, 199–207, (1994).

Craig A. Mullen, et al., "Transfer of the Bacterial Gene for Cytosine Deaminase to Mammalian Cells Confers Lethal Sensitivity to 5-fluorocytosine: A negative selection system", *Proc. Natl. Acad. Sci. USA*, 89, 33–37, (1992).

Elizabeth G. Nabel, et al., "Site–Specific Gene Expression in Vivo by Direct Gene Transfer into the Arterial Wall", *Science*, 249, 1285–1288, (1990).

H. P. Noguiez, et al., *PNAS*, 93, 4175, (1996).

B. W. O'Malley, et al., *Can Res.*, 56, 1737, (1996).

E. H. Oldfield, et al., *Hum. Gene Ther.*, 6, 55, (1995).

Jack Price, et al., "Lineage Analysis in the Vertebrate Nervous System by Retrovirus–mediated Gene Transfer", *Proc. Nat'l. Acad. Sci. USA*, 84, 156–160, (1987).

Z. Ram, et al., *J. Neurosurg.*, 81, 256, (1994).

R. Ramesh, et al., "In vivo analysis of the "bystander effect" a cytokine cascade", *Experimental Hematoogy*, 24, 829–838, (1996).

Melissa A. Rosenfeld, et al., "In Vivo Transfer of the Human Cystic Fibrosis Transmembrane Conductance Regulator Gene to the Airway Epithelium", *Cell*, 68, 143–155, (1992).

R. J. Samulski, et al., "Targeted Integration of Adeno–associated Virus (AAV) into Human Chromosome 19", *EMBO J.*, 10, 3941–3950, (1991).

W. Roy Smythe, et al., "Treatment of Experimental Human Mesothelione Using Adenovirus Transfer of the Herpes Simplex Thymidine Kinase Gene", *Annals of Surgery*, 222, 78–86, (1995).

E. J. Sorscher, et al., *Gene Therapy*, 1, 233–238, (1994).

Leslie D. Stratford–Perricaudt, et al., "Evaluation of the Transfer and Expression in Mice of an Enzyme–Encoding Gene Using a Human Adenovirus Vector", *Human Gene Ther.*, 1, 241–256, (1990).

H. Su, et al., *Hum. Gene Ther.*, 7, 463, (1996).

S. Suguya, et al., *Hum. Gene Ther.*, 7, 223, (1996).

Y. Takamiya, et al., "An Experimental Model of Retrovirus gene therapy for malignant brain tumors", *J. Neurosurg.*, 79, 104–110, (1993).

Y. Takamiya, et al., "Gene Therapy of Malignant Brain Tumors: A Rat Glioma Line Bearing the Herpes Simplex Virus Type 1–Thymidine Kinase Gene and Wild Type Retrovirus Kills Other Tumor Cells", *J. Neurosci. Res.*, 33, 493–503, (1992).

Robert I. Tepper, et al., "Murine Interleukin–4 Displays Potent Anti–Tumor Activity In Vivo", *Cell*, 57, 503–512, (1989).

Pierre Thiberghien, "Use of suicide genes in gene therapy", *J. of Leukocyte Biology*, 56, 203–209, (1994).

X. W. Tong, et al., *Gyn. Onc.*, 61, 175, (1996).

R. G. Vile, et al., *Can. Res.*, 54, 6228, (1994).

R. G. Vile, et al., *Cancer Res.*, 53, 3860, (1993).

Alkhatib, G., et al., "High–level eucaryotic In Vivo expression of biologically active measles virus hemagglutinin by using an adenovirus Type 5 helper–free vector system", *Journal of Virology*, 62(8), 2718–2727, (Aug. 1988).

Ballay, A., et al., "In vitro and in vivo synthesis of the hepatitis B virus surface antigen and of the receptor for polymerized human serum albumin from recombinant human adenoviruses", *EMBO Journal*, 4 (13B), 3861–3865, (Dec. 30, 1985).

Berkner, K.L., "Development of adenovirus vectors for the expression of heterologous genes", *BioTechniques*, 6(7), 616–629, (Jul.–Aug. 1988).

Berkner, K.L., et al., "Abundant expression of polyomavirus Middle T antigen and dihydrofolate reductase in an adenovirus recombinant", *Journal of Virology*, 61(4), 1213–1220, (Apr. 1987).

Davidson, D., et al., "Overproduction of polyomavirus middle T antigen in mammalian cells through the use of an adenovirus vector", *Journal of Virology*, 61(4), 1226–1239, (Apr. 1987).

Fuerst, T.R., et al., "Transfer of the inducible lac repressor/operator system from Escherichia coli to a vaccinia virus expression vector", *Proc. Natl. Acad. Sci. USA*, 86, 2549–2553, (Apr. 1989).

Gluzman, Y., et al., "Helper–free adenovirus type–5 vectors", *Eukaryotic Viral Vectors, Y. Gluzman, Ed., Cold Spring Harbor Laboratory*, 187–192, (1982).

Hermonat, P.L., et al., "Use of adeno–associated virus as a mammalian DNA cloning vector: Transduction of neomycin resistance into mammalian tissue culture cells", *Proc. Natl. Acad. Sci. USA*, vol. 81, 6466–6470, (Oct. 1984).

Johnson, D.C., et al., "Abundant expression of herpes simplex virus glycoprotein gB using an adenovirus vector", *Virology*, 164(1), 1–14, (May 1988).

Kieny, M.P., et al., "Expression of rabies virus glycoprotein from a recombinant vaccinia virus", *Nature*, 312(5990), 163–166, (Nov. 8–14, 1984).

Lubeck, M.D., et al., "Immunogenicity and efficacy testing in chimpanzees of an oral hepatitis B vaccine based on live recombinant adenovirus", *Proc. Natl. Acad. Sci. USA*, vol. 86, 6763–6767, (Sep. 1989).

McLaughlin, S.K., et al., "Adeno–associated virus general transduction vectors: analysis of proviral structures", *Journal of Virology*, 62(6), 1963–1973, (Jun. 1988).

Molnar–Kimber, K.L., et al., "Characterization and assembly of hepatitis B envelope proteins expressed by recombinant adenovirus", Hepadna Viruses: Proc. of a Director's Sponsors—UCLA Symposium, W. Robinson et al., Eds., Liss, pub., New York, 173–187, (Mar.–Apr. 1987).

Morin, J.E., et al., "Recombinant adenovirus induces antibody response to hepatitis B virus surface antigen in hamsters", *Proc. Natl. Acad. Sci. USA*, 84, 4626–4630, (Jul. 1987).

Palella, T.D., et al., "Herpes simplex virus–mediated human hypoxanthine–guanine phosphoribosyltransferase gene transfer into neuronal cells", *Molecular & Cellular Biology*, 8(1), 457–460, (Jan. 1988).

Rasmussen, C.D., et al., "Methods for analyzing bovine papilloma virus–based calmodulin expression vectors", *Methods in Enzymology*, 139, 642–654, (1987).

Roizman, B., et al., "Genetic engineering of novel genomes of large DNA viruses", *Science*, 229(4719), 1208–1214, (Sep. 20, 1985).

Saito, I., et al., "Novel RNA family structure of Hepatitis B virus expressed in human cells, using a helper–free adenovirus vector", *Journal of Virology*, 58(2), 554–560, (May 1986).

Yamada, M., et al., "Overproduction of the protein product of a nonselected foreign gene carried by an adenovirus vector", *Proc. Natl. Acad. Sci. USA*, 82(11), 3567–3571, (Jun. 1985).

CANCER THERAPY UTILIZING EX VIVO GENE TRANSDUCTION

This is a divisional of application Ser. No. 08/351,891 filed Dec. 8, 1994, now U.S. Pat. No. 5,601,818; which, in turn, is a continuation of application Ser. No. 07/919,027, filed Jul. 23, 1992, now abandoned; which is a Continuation-in-Part of U.S. patent application Ser. No. 07/736,391, filed Jul. 26, 1991, now abandoned.

The present invention was made with the support of the Government under NIH Grant No. AI00697. The U.S. Government has certain rights in the invention.

BACKGROUND OF THE INVENTION

Therapies designed to cure or prevent the progression of cancer are often based on biological or metabolic differences between normal and malignant cells. Many cancers are characterized by unrestricted or abnormal growth of the cancer cell population at the expense of host cells and tissues. The relatively rapid cancer cell growth rate compared to normal cells requires high levels of metabolic activity on the part of the cancer cells. One activity associated with malignant cells, the high rate of deoxyribonucleic acid (DNA) replication as compared with that of most normal cells, has been extensively examined as a potential target for therapeutic approaches to treat cancer. Thus, there has been a great deal of effort directed toward the development of therapeutic agents or treatments that preferentially kill malignant cells by interfering with one or more aspects of their DNA replication. Such approaches have met with some success, but because such therapies are often nonspecific, normal host cells with high growth rates, such as bone marrow cells, are also susceptible to killing by the same agent or therapy. The toxicity of cancer therapies toward normal cells often leads to severe side effects and limits their ultimate efficacy.

Another difficulty related to cancer treatment centers on the characteristic spread or metastasis of cancer cells to sites distant from the origin of the initial cancer cell. Advanced stages of cancer are often associated with malignant growths at multiple sites. Such spreading often complicates or prevents the successful treatment of cancer by surgical means.

The difficulties related to the design of effective therapies for cancer has spurred intense research directed toward understanding the molecular basis of cancer and its development from normal cells. This research has led to an understanding of some of the biological events that lead to full-blown malignancy starting from a normal cell. Land et al., *Science,* 222, 771 (1983) summarized research findings that implicated cellular oncogenes in the development of cancer. Additional subsequent efforts have been directed toward understanding the function of oncogenes at a molecular level. Activated oncogenes have been used to construct animal models of cancer development, further substantiating their role in the etiology of cancer (Hanahan, *Ann. Rev. Genet.,* 22, 479 (1988)). This knowledge has created an awareness that activated oncogenes appear to represent targets for therapeutic intervention in cancer therapy (Huber, *Fed. Amer. Soc. Exper. Biol. J.,* 3, 5 (1989)). For example, Drebin et al., *Cell,* 41, 695 (1985) demonstrated that modulation of the neu oncogene protein by monoclonal antibodies to the surface of transformed cells reversed the transformed phenotype of tumor cells in vitro. However, it is becoming clear that while activated oncogenes represent potential therapeutic targets for cancer therapy, the differences between them and their normal cellular counterparts are often subtle. The subtle differences suggests that development of specific and effective therapies, without toxic side effects, will prove to be difficult. The fundamental similarity between malignant and normal cells renders malignant cells only somewhat more susceptible to killing based on therapies that affect targets or activities that both cell types share.

An alternate approach to the development of tumor-specific therapy has been adduced wherein a metabolic difference is artificially introduced into cancer cells that renders them susceptible to killing by a therapeutic agent (Moolten, *Can. Res.,* 46, 5276 (1986)). This concept, the mosaic strategy, requires prophylactic generation of mosaicism in tissues that may in the future become cancerous (Moolten, *Med. Hypotheses,* 24, 43 (1987)). The success of the strategy relies on tumor cells differing from normal cells by carrying an inserted gene that confers either drug susceptibility to the malignant cells or drug resistance to the normal cells. The aim of creating mosaicism is to artificially create a significant metabolic difference between normal and malignant cells. This difference then serves as a therapeutic target for effective malignant cell killing with minimal toxicity to normal cells. Because cancer often results from proliferation of a single transformed cell, all of the cells in a given case of cancer will tend to be identical or clonal (Fialkow, *Biochim. Biophys. Acta,* 458, 283 (1976)). If, prior to the development of a malignant cell, a drug susceptibility gene was inserted into that same cell, then all of the cells associated with the ensuing cancer would be susceptible to the appropriate therapeutic agent. Cells in the subject that did not receive the drug sensitivity gene would be resistant to the drug. Thus, mosaic strategy clearly represents a prophylactic application of transduced cells for therapeutic use.

The basic concept of the mosaic model approach has not yet been demonstrated in vivo because generation of malignant cells from normal transduced cells in vivo has not been observed. Insertion of the herpesvirus thymidine kinase (TK) gene into mammalian cells renders them sensitive to the nucleoside analog ganciclovir (GCV). GCV toxicity is conferred by enzymatic activity of the TK gene which metabolically activates GCV in cells (Nishiyama et al., *J. Gen. Virol.,* 45, 227 (1979)). The activated GCV is toxic to cells and kills them. The TK gene by itself is not lethal to cells in the absence of GCV. Mouse tumor cell lines containing the TK gene were shown to give rise to tumors in vivo in mice. Tumor regression occurred if GCV was administered to the mice, while control mice that did not receive GCV failed to survive the progression of cancer (Moolten, *Can. Res.,* 46, 5276 (1986)). Subsequent experiments with retroviral vectors carrying the TK gene were used to transfer TK enzyme activity to tumor cell lines in tissue culture. One mouse tumor, a sarcoma, was then shown to be sensitive to GCV therapy in vitro and in vivo (Moolten and Wells, *J. Natl. Cancer Inst.,* 82, 297 (1990)). These experiments demonstrated the feasibility of killing tumor cells in vivo by using genetic engineering to create a target for cancer chemotherapy.

However, as pointed out by the authors of those experiments (Moolten, *Can. Res.,* 46, 5276 (1986); Moolten, *Med. Hypotheses,* 24, 43 (1987); Moolten et al., *J. Natl. Cancer Inst.,* 82, 297 (1990), the mosaic strategy suffers from a number of drawbacks and cannot be used in human subjects with the existing technology for genetically engineering cells. A current limitation associated with gene therapy using retroviral vectors is the inefficient transfer of genes to long-lived normal stem cells in humans (Eglitis et al.,

*Biochem. Biophys. Res. Commun.,* 151, 201 (1988)). Retroviral vectors are the most efficient vehicles in current use for the transfer of exogenous genes into mammalian cells (Eglitis et al., *Biotechniaues,* 6, 608 (1988)). Another limitation associated with retroviral vectors when used in vivo as envisioned in the mosaic strategy, is their limited and transient expression of inserted genes after introduction of the genetically-engineered cells into animals (Anderson et al., *Cold Spring Harbor Symp. Quant. Biol.,* 51, 1073 (1986)). Successful application of the mosaic model to cancer treatment requires that a gene inserted in vivo will continue to express at a later time, possibly years later, when tumors arise from mosaic tissues. Another requirement of the mosaic strategy is the efficient infection of a relatively high proportion of stem cells that may later give rise to a tumor. If stem cells are inefficiently infected, then the probability that a tumor will arise from a genetically-engineered cell is low. Current technologies for long-term in vivo gene expression of inserted genes and for efficient widespread gene transfer to cells in human subjects are not currently available.

Other disadvantages of the mosaic model include stringent safety requirements for vectors used for gene therapy in healthy human subjects (Moolten, *Med. Hypotheses,* 24, 43 (1987); Anderson, *Science,* 226, 401 (1984)) or the need to insert genes into stem cells, which cells are poorly defined and difficult to genetically manipulate (Anderson et al., *Cold Spring Harbor Sym. Quant. Biol.,* 51, 1073 (1986)). These considerations prevent the application of the mosaic strategy for cancer chemotherapy in the near future as pointed out by Moolten et al., *J. Natl. Cancer Inst.,* 82, 297 (1990).

Another approach to cancer therapy that relies on retroviral-mediated gene transfer is described in a patent application entitled "Gene Therapy," (U.S. Ser. No. 07/365, 567, NTIS publication No. PB89-206155). This approach describes the use of retroviral vectors that carry either marker or therapeutic genes for genetically-engineering immune cells that fight against cancer in a subject. The genetically-engineered cells in this case are tumor infiltrating lymphocytes (TIL) which are believed to mediate cytotoxic immune responses against certain cancers (Rosenberg et al., *New Engl. J. Med.,* 316, 889 (1987)). The TIL are explanted from tumors in human subjects and grown in tissue culture in vitro. Following growth in tissue culture, the cells are transduced with a retroviral vector, selected for growth of only those TIL that express vector genes and then reinfused back into patients. One aspect of the approach is the potential to use the genetically-engineered TIL to target or return to the tumors in vivo, after the TIL are returned to the subject.

Therefore, a need exists for effective methods of cancer therapy employing the techniques of genetic engineering to render populations of cancer cells susceptible to destruction with agents that do not adversely affect normal cells.

SUMMARY OF THE INVENTION

The present invention provides a method for eliminating cancer cells from a population of cells containing cancer cells and noncancerous cells (i.e., "tumor" or "malignant" cells and "normal" cells), comprising:

(a) providing a mixture of noncancerous cells and cancer cells;

(b) contacting the cancer cells with transgenic cancer cells comprising a foreign gene that renders the transgenic cancer cells substantially more susceptible to a therapeutic agent than the cancer cells or the noncancerous cells; and (c) contacting the transgenic cancer cells with an amount of the therapeutic agent effective to kill an amount of said transgenic cancer cells that is effective to result in the killing of a substantial portion of said cancer cells, while not substantially damaging said noncancerous cells.

When conducted in vitro, the present method can be used to eliminate cancer cells from normal cells in tissue culture. For example, cancer cells can be eliminated from human bone marrow from patients who are to receive an autologous bone marrow transplant. However, in a preferred embodiment, the present method is employed to treat cancer, e.g., by causing remission and/or elimination of cancer in human or animal subjects so afflicted. In the course of the present treatment, a portion, or population, of the cancer cells of the human or animal cancer patient or "subject" can be explanted, and transformed with the foreign gene or genes to yield a population of genetically-engineered or transgenic cancer cells having the desired susceptibility to the therapeutic agent or agents. Useful transformation methods include transfection, electroporation or liposome delivery of the foreign gene(s). The transgenic cancer cells can then be reimplanted into the subject, preferably at or adjacent to the tumor mass or masses. Alternatively, a population of the subject's cancer cells can be transformed in situ, to induce the desired susceptibility, by direct injection, of either "naked" DNA comprising the foreign gene or of the liposome-encapsulated gene.

As used herein, the term "transgenic" means that the cancer cells are transformed by the techniques of genetic engineering so as to contain at least one gene or gene fragment in addition to, or in place of, the normal genetic complement or genome of the cell. The term "foreign" as used with respect to the gene used to transform the cancer cells means that the gene (or gene fragment) is obtained from a source that is different from the genome of the target or "parent" cancer cell, e.g., from a bacterium or a virus, preferably a retrovirus. The term "foreign gene" also includes completely synthetic genes or gene fragments. The foreign gene is preferably introduced into the cancer cell on a vector, such as a plasmid vector or a viral vector, most preferably a retroviral vector, that also comprises a promoter, such as SV40, operably linked to the gene so as to enhance expression of the gene following transformation, and optionally, a selectable marker gene, such as neo, hpt, or aphII, to assist in the identification and insolation of transgenic cancer cells.

Surprisingly, it has been found that the "hybrid cancer" that results from introducing the transgenic cancer cells into the subject can be eliminated, or forced into remission, by administering to the subject an amount of a therapeutic agent or agents effective to kill at least a portion of the transgenic cancer cells. The therapeutic agent can be a bioactive chemical entity (a "drug") or radiation, such as UV light or gamma irradiation. Destruction of a sufficient number of the transgenic cancer cells initiates a chain of events, at least some of which are mediated by the subject's immune system, that leads to the destruction of at least a portion of the nontransgenic cancer cells. Surprisingly, the number of transgenic cancer cells need not exceed, or even equal, the number of nontransgenic cancer cells. Furthermore, the cancer cells transformed by the foreign gene need not be identical in lineage to the "parent" cancer cells sought to be eliminated, e.g., from the subject, but can be derived from an in vitro-established line of the same, or a different type of cancer cell.

Preferred genes for imparting susceptibility of cancer cells to therapeutic agents, such as drugs, are introduced into cancer cells on retroviral vectors, and may be retroviral genes or gene fragments, such as the preferred thymidine kinase gene of herpes simplex virus type 1 (HSV-TK). The expression of this gene renders the transgenic cancer cells susceptible to eradication by ganciclorvir, an antiviral nucleoside analog. As used herein with respect to transgenic cancer cells, the term "substantially more susceptible to a therapeutic agent" means that the agent has a therapeutic index ($TI_{50}$) which is sufficiently high so that transgenic cancer cells are killed without damaging normal noncancerous cells (or, directly, the cancerous cells), to the extent that measurable remission of the cancer occurs, without threatening the life of the afflicted subject. $TI_{50}$'s of about 10 to 200–500 or above can be achieved during the practice of the present invention.

Although the present invention is exemplified by reference to ganciclovir, other anti-viral nucleoside analogs are known to the art, and may be employed in the present invention, including vidarabine, acyclovir, AZT, carbovir, ddI, ddC, ribavirin and the like. Representative compounds of this class of therapeutic agent are disclosed, e.g., in U.S. Pat. Nos. 4,931,559; 3,917,837; 3,817,982; 4,724,232 and in published European patent application nos. 349,242; 236,935; 311,100; 316,017; and 369,409. Non-nucleoside antivirals can also be employed in the present invention. The present method can also be used to enhance the therapeutic index of other known classes of cytotoxic drugs, so that they can be used to effectively eliminate cancer cells. A discussion of these drugs is found in U.S. Pat. Nos. 4,938,949 and 5,035,878.

The present invention can also employ transgenic cancer cells having a foreign gene for a cytokine or lymphokine. Transgenic cancer cells with a cytokine gene can be employed alone or in combination with the above-described transgenic cancer cells having a foreign gene imparting cancer cell susceptibility to a therapeutic agent. Alternatively, transgenic cancer cells having both the foreign gene imparting drug susceptibility and a cytokine gene can be used. A preferred cytokine gene to be incorporated into the transgenic cancer cell is exemplified by interleukin-1 (IL-1), IL-2, IL-4, IL-6, alpha interferon and gamma interferon. By way of example only, a transgenic cancer cell having a retrovirus carried IL-1 gene can be employed together with a transgenic cancer cell having the HSV-TK gene. The combination of these transgenic cancer cells can be used to kill substantial amounts of transgenic and non-transgenic cancer cells without damaging normal non-cancerous cells. The cytokine gene can also be introduced to a transgenic cell together with a retroviral gene or gene fragment, as for example, HSV-TK, thereby providing transgenic cancer cells exhibiting both therapeutic agent susceptibility and cytokine activity useful to provide enhanced killing ability of cancer cells.

In the practice of the present invention, it is also preferred to proliferate, or expand, the population of transgenic cancer cells in vitro, prior to administering them to the subject. In some cases, the ex vivo population obtained from the subject, and transformed, may be supplemented with transgenic cancer cells from another source. It is also preferred to irradiate the transgenic cancer cells with a "lethal" dose of gamma radiation, so that the population employed as the therapeutic dosage is viable, but unable to replicate.

Generally, any cell type can act as a recipient for insertion of a selected gene or genes. These transgenic cells can act in vivo or in vitro (i) to target tumors or malignant cells and (ii) to provide a cell population that is susceptible to a therapeutic agent or treatment. When administered to a subject, the transgenic cells render both the unmodified or resistant tumor cell population and the transgenic cells susceptible to cancer therapy.

Another aspect of the present invention provides a method for the immunization of a subject against cancer that comprises, (i) introduction of a gene or genes into a population of cancer cells to yield a population of genetically-engineered cells; (ii) expanding the population of the genetically-engineered cells in vitro; (iii) implanting a unit dose of the population of the cells into the subject and (iv) administering to the subject an agent that is toxic to the implanted population of cells so that both the implanted population of cells and unmodified tumor or cancer cells are killed.

DETAILED DESCRIPTION OF THE INVENTION

Definitions of terms used herein are as follows. The term, "subject" refers to both humans and animals. The term "parental cells" refers to those cells that serve as a source of cells directly from a subject or from a cell line grown in tissue culture that is identical to the subject tumor cells. "Parental cells" are essentially genetically and phenotypically identical to daughter cells produced therefrom, e.g., they comprise the same cell surface antigens that are involved in the (i) immune response in a subject that leads to killing of those cells and (ii) recognition of parental cells by daughter cells in vivo. The term "daughter cells" refers to transgenic cells that are genetically engineered in order to insert a gene or genes that confer susceptibility upon the resultant transgenic cells to a therapeutic agent. Daughter cells are derived from parental cells and are essentially identical genetically to parental cells except for the inserted gene(s) or gene fragments. "Carrier cells" refer to any cell line, either transformed or nontransformed, which contain one or more genes that can confer susceptibility upon the cells to at least one therapeutic agent. For example, "carrier cells" need not be derived from "parental cells," so long as their destruction leads to the death of a class of parental cells. For example, mouse fibrosarcoma cells can be used to kill mouse breast tumor cells and a human ovarian cell line can be used to treat mouse fibrosarcomae. "Hybrid cancer" or "hybrid tumor" refers to a cancer or tumor in a subject that consists of a mixed population of parental and either daughter or carrier cells. Parental and daughter or carrier cells need not necessarily be derived from the same subject; a wide variety of cell lines may be used to generate either daughters or carriers. "In vivo" refers to cells or events present or occurring in the subject and "in vitro" refers to cells or events present or occurring in tissue culture. "Susceptibility gene(s)" refers to (i) a gene(s) that directly or indirectly renders cancer cells that carry and express such gene(s) susceptible to exogenously administered therapeutic agents, (ii) a gene(s) that elicits or enhances an immune response in a subject that leads to killing of both daughter or carrier and parental cells or (iii) a gene(s) that elicits any response in the subject that facilitates killing of both daughter or carrier and parental cells.

The present invention is based on the finding that when a hybrid cancer or tumor is generated by implanting a mixture of parental and daughter cells into a subject, such as an animal host, and subsequently administering a therapeutic agent toxic to the daughter cells leads to the killing of parental cells as well as the daughter or carrier cells. Killing of cancer cells in a subject, wherein the cells consist of a cell population of daughter cells only, in this manner has been demonstrated by Moolten et al., *J. Natl. Cancer Inst.*, 82, 297 (1990), as discussed supra. However, it has surprisingly been found that treatment of a hybrid tumor or cancer condition also can lead to complete regression of the tumor or cancer in a subject, after administration of an appropriate therapeutic agent to the subject having the hybrid cancer or tumor. This finding, when applied in the context of therapeutic applications, permits the specific killing of hybrid cancer cell populations in a subject by the use of a therapeutic agent that has relatively low toxicity toward normal, noncancerous cells in the subject. The killing of parental cells is believed to be due in part to immune responses induced in the subject. However, additional mechanism(s) of killing of parental cells in the subject may also be partly responsible for parental cell killing.

Parental cell killing may be related to necrosis or apoptosis. Necrosis is characterized by swelling of the cell, disintegration of the cell membrane and nuclear flocculation. Apoptosis is characterized by cell shrinkage, membrane vesicle formation and condensation of chromatin (Cotter et al., Anticancer Research, 10, 1153 (1990)). Killing of parental cells may be due in part to death of daughter or carrier cells by apoptosis, resulting in tumor "immunity" in a subject.

As described above, the mosaic strategy for cancer therapy relies on gene transfer and expression technology that is not currently available since it relies on gene transfer into normal cells that may subsequently become malignant. (Moolten et al., J. Natl. Cancer Inst., 82, 297 (1990); Moolten, Med. Hypotheses, 24, 43 (1987)). Current gene therapy approaches for various disease states rely on insertion of genes into lymphocytes or other normal cells such as epithelial cells (Morgan et al., U.S. Pat. No. 4,868,116). The present invention differs from these approaches in that it utilizes cells that are malignant to carry an inserted gene into a subject. Another approach to cancer therapy, described by Gottlieb (U.S. Pat. No. 4,874,608), relies on the use of agents that are administered in order to enhance a subject's immune response against malignant cells. The present invention utilizes cancer cells to generate an in vivo response that may have an immune component as part of the subjects' response against malignant cells. Other related approaches meticulously eliminate cancer cells from the therapeutic protocol before administering genetically-engineered cells to a subject (Rosenberg et al., New Engl. J. Med., 316, 889 (1987)).

Previous work has demonstrated that the effectiveness of immunization of a subject is affected by the type of antigen that is used. However, it is generally found that immunization of a subject is most effective when the antigen used for immunization closely resembles the native antigen present in the "target" pathogen. In the current invention, live cancer cells may serve as an immunogen to stimulate a specific immune response against the cancer cells. Although alive, the carrier cancer cells used are preferably not be capable of cell division when used in vivo. Live, nonreplicating carrier cells may be conveniently be obtained by lethal irradiation. The method described herein is thus conceptually counter to current approaches toward cancer therapy by utilizing live malignant cells for therapeutic benefit. The present invention also utilizes presently-available gene transfer technology for exploiting gene expression in subjects shortly after implantation of genetically-engineered or "transgenic" cells into a subject for therapeutic benefit. This method thus places less stringent demands on existing gene transfer and expression technology because expression of a gene(s) inserted into cells in a subject is required only for a short period of time, i.e., during administration of an appropriate therapeutic agent to effect killing of susceptible daughter cells, and thus to initiate the therapeutic process.

The present invention can thus be widely utilized for the treatment of various animal or human cancers or malignancies, including cancers associated with hematopoietic cells, central nervous system cells, lung cells, breast cells, ovary cells and liver cells. Specific human cancers amenable to treatment include melanoma, colon cancer, ovarian cancer, pancreatic cancer, stomach cancer, neuroblastoma, squamous cell carcinoma, fibrosarcoma and leukemia. Because the genetically-engineered daughter cells described herein are designed to be extremely sensitive to a preselected drug or non-drug therapy, minimal toxicity to normal subject cells and tissues occurs during the course of drug treatment or other therapy that is used to kill the daughter cells in the subject.

Preferred embodiments of the present invention employ retroviral vectors to transfer a gene imparting drug susceptibility into a population of cancer cells. The preferred vectors used herein are designated STX, $\mu$TS, pIL1, LASN and LNL. The STK vector carries genes that encode the neomycin phosphotransferase gene (Neo) from the bacterium Escherichia coli and the thymidine kinase gene (TK) from human herpes simplex virus type 1. TK genes from other viral sources could be utilized in place of the HSV TK gene in STK. The Neo gene was expressed via the LTR promoter and the TK gene was expressed via the SV40 virus early promoter as described by Moolten et al., J. Natl. Cancer Inst., 82, 297 (1990). The TX gene renders mammalian cells that express the TX protein susceptible to killing by the anti-viral nucleoside ganciclovir (GCV) as described above (Moolten and Wells, J. Natl. Cancer Inst., 82, 297 (1990)). The STK vector thus served to transfer a drug susceptibility gene into malignant parental cells in order to generate malignant daughter or carrier cells. Cells carrying the Neo gene are also resistant to killing by the neomycin analog, G418, which is toxic to mammalian cells that do not express the Neo protein. The Neo gene permits growth of cell populations wherein all cells contain and express the vector by growing the cells in the presence of G418. This ensures that all cells that lack the vector are killed before subsequent studies are carried out in subjects. The LNL vector carries only the Neo gene and serves as a control to show that the effects observed in subjects are not due to the presence of either vector sequences or to the presence of the npt. The $\mu$TK vector is similar to the STK vector except that the TK gene is expressed via the herpesvirus TK promoter as described by Moolten et al., J. Natl. Cancer Inst., 82, 297 (1990).

It has been found that employing transgenic cells having a cytokine gene together with transgenic cancer cells having a gene imparting drug susceptibility is useful. Additionally, a retroviral vector including both the gene imparting drug susceptibility and a cytokine gene such as interleukin, an interferon, or the like, can be used to produce a useful transgenic cancer cell with both drug susceptibility and cytokine activity.

Introduction of vector sequences into parental cells can be achieved by a process known as transduction, e.g., as disclosed by Moolten et al., J. Natl. Cancer Inst., 82, 297 (1990). Transduction was carried out using various tumor cell lines comprising either the STK vector or the LNL control vector. Thus, two different transgenic cell lines, one carrying the TK (and Neo) gene and a control line carrying only the Neo gene, were derived by transduction from each primary tumor cell line. The resultant LNL transgenic tumor cell lines (LNL cells) were used as parental cells and the resultant STK transgenic tumor cells (STK cells) were used as daughter cells. Injection of syngeneic mice with either LNL cells, STK cells or mixtures of both LNL and STK cells was followed by administration of GCV, and the course of cancer progression or arrest (induced by GCV) in mice was followed. It was found that mixtures of 90% STK cells and 10% LNL cells were efficiently suppressed by GCV therapy in mice. Surprisingly, mixtures that consisted of 50% each of STK and LNL cells were also effectively killed in mice by GCV therapy. In all cases, control animals receiving the same cell types but not treated with GCV experienced cancer progression as measured by tumor growth and/or death of the subject animal. Control animals containing tumors consisting of 100% LNL cells that were treated with GCV also experienced unchecked tumor growth.

Further investigation was carried out to determine the nature of the mechanism responsible for killing of the normally GCV-resistant LNL cells. A presence of an immune component was discovered that apparently kills the LNL cells. This was demonstrated by implanting STK cells into mice and administering GCV until the STK cells were killed. Six to eight weeks later, additional STK cells were implanted into the same mice and the progression of cancer was followed without administration of GCV. It was discovered that in the majority of animals tested, tumor progression did not occur. Control animals that were not previously challenged with STK cells and GCV experienced tumor growth as expected. The presence of an immune component was further demonstrated by conducting the same experiment using mice sublethally (500 rads) irradiated to reduce their immune responses. These animals, when challenged with STK cells, could not eliminate the STX tumors after administration of GCV in all cases.

The success of the present therapeutic method appears to depend at least partially on (i) the mechanism of tumor cell death initiated by the drug treatment and (ii) an immune response elicited in the host after introduction of the genetically engineered tumor cells. As described above, malignant and the corresponding normal cells tend to have only minor or subtle differences between them. Once an immune or physical response to daughter or carrier cells has been initiated, parental cells also become vulnerable to the response. In view of (i) the close similarity of malignant cells to normal cells and (ii) the effectiveness of the response elicited by the methods disclosed herein, cells in a human or animal subject, or in tissue culture, that are malignant or otherwise diseased (such as virally infected) are candidates for elimination via the present therapeutic approach. For example, cells infected with pathogenic human viruses usually express one or more cell surface antigens that mark the infected cells. These antigens are foreign to the subject's genome and can thus serve as tags that lead to cell death after the killing response is generated in the host using the present method. Antigens that are often associated with human cancers, such as the carcinoembryonic antigen, may also be inserted into malignant cells in order to generate a population of daughter cells that will elicit, in a subject, an effective host response that will kill both parental and daughter cells.

Other mechanisms, in addition to an immune response, appear to be involved in target cell killing. Mixtures of 50% LNL and 50% STK cells in tissue culture are killed when GCV is added to the culture medium. A non-immunologic component must also exist because no immune cells are present in the mixed cell populations in vitro. The mechanism may be related to the manner of cell death induced by the GCV treatment. Cells dying in response to GCV were shown to expire by the process of apoptosis. During apoptosis, tumor cells break down into apoptotic vesicles. The vesicles can be phagocytized by parental tumor cells. Thus, the carrier cells expressing TK may die after exposure to GCV, generating vesicles which contain the TK enzyme and which are phagocytized by parental tumor cells. Once inside parental cells, the TK enzyme converts GCV to a form that is toxic to the parental tumor cells. In addition, a significant amount of toxic GCV metabolite in the daughter cells may be transferred into parental cells in vesicles which then can contribute to killing the parental cells.

Another aspect of the present invention is the homing of daughter cells to parental cells in vivo. Although a cell-mediated response appears to be responsible for the long-term immunization of animals after challenge with daughter cells followed by their elimination by GCV, the killing of both daughter and parental tumor cells by GCV within a few days after GCV was administered, shows that another mechanism is responsible for tumor cell killing. The rapid cell killing after GCV therapy was initiated showed that tumor cell killing responses in the subjects occurred before known cell-mediated responses could be established. The parental tumor cell killing was due to homing of daughter cells to resident parental tumor cells. This was demonstrated by injection of parental cells 24 hours prior to injection of daughter cells into a subject and subsequent initiation of GCV therapy. The rapid and reproducible killing of both parental and daughter cells demonstrates that the subject can kill all tumor cells before a classical cell mediated immune response was established. The precise nature of the cell killing response by the subject is not fully understood at a molecular level, but probably involves homing of daughter cells to parental cells in the subject. The ability of malignant cells to migrate or metastasize is the phenomenon whereby cells of the same type tend to aggregate or grow together both in vitro and in vivo. In the present case, daughter cells may migrate to parental cells resident in the subject and, after initiation of GCV therapy, lead to rapid killing of the parental cells by the subject.

Any method that can generate a daughter cell population will lead to the desired results in vivo. The use of such methods involves direct introduction of an appropriate gene (s) into a tumor in vivo. If, for example, a viral vector can infect a sufficient number of tumor cells after in vivo administration, then an appropriate daughter cell population can be generated in vivo without the need to explant tumor cells from the subject for genetic manipulations in vitro. Other methods of direct in vivo gene transfer have been described, e.g., by Wolff et al., in *Science*, 247, 1465 (1990), that can be used to generate a sufficient population of daughter cells in vivo, without the need to explant tumor cells for genetic manipulation in vitro. The present method may also be used together with conventional cancer therapies in order to enhance overall therapy efficacy.

The present invention is described by reference in the following detailed examples.

EXAMPLE 1
In Vitro Toxicity of GCV for WEHI-STK Cells
Cell Proliferation Assay.

The WEHI murine myelomonocyte tumor cell line [American Type Culture Collection (ATCC) No. TIB 68], derived from BALB/c mice, was transduced with the STK vector. The viral stock used for transduction was derived from producer cell lines derived from either PA317 or psi-2 packaging cell lines, which were grown to 70–90% confluence in tissue culture flasks. Fresh medium was added and 16–20 hours later, the viral stock was isolated. The WERI line was grown in viral stock with 8 μg/ml polybrene for 24 hours, at which time the cells were placed in fresh medium. Twenty-four hours later, the transduced cells were selected for in G418 (Geneticin, GIBCO, Inc.) at a concentration of 200–2000 μg/ml, depending on the cell type. The transduced cells were grown in standard tissue culture medium, Dulbeccos Modified Eagle's Medium with 10% fetal calf serum and glutamine (DMEM), supplemented with 0.8 mg/ml of G418 in order to select for a population of cells that all carry and express the STK vector. See Mann et al., *Cell*, 33, 153 (1983). The resulting cell population, WEHI-STK, was then tested for sensitivity to exposure to GCV in tissue culture. Transgenic WEHI-STK cells ($1 \times 10^5$) were plated on 35 mm tissue culture plates 24 hours prior to exposure to GCV for either 24 or 72 hours. Following GCV treatment, the cells were assayed for proliferation by measuring $^3$H-thymidine uptake. The results shown in Table 1 demonstrated that the WEHI-STK cells were sensitive to GCV exposure and control WEHI cells were relatively insensitive. The results are expressed as a percentage of cell proliferation compared to control WEHI cells not exposed to GCV.

TABLE 1

| | cell line | GCV concentration (μM) | proliferation (%) |
|---|---|---|---|
| 24 hour exposure | WEHI | 0.005 | 100 |
| | | 0.05 | 95 |
| | | 0.5 | 90 |
| | | 5.0 | 90 |
| | | 50 | 80 |
| | WEHI-STK | 0.005 | 100 |
| | | 0.05 | 80 |
| | | 0.5 | 50 |
| | | 5.0 | 15 |
| | | 50 | 8 |
| 72 hour exposure | WEHI | 0.005 | 100 |
| | | 0.05 | 90 |
| | | 0.5 | 95 |
| | | 5.0 | 90 |
| | | 50 | 60 |
| | WEHI-STK | 0.005 | 100 |
| | | 0.05 | 80 |
| | | 0.5 | 13 |
| | | 5.0 | 1 |
| | | 50 | 0.6 |

EXAMPLE 2

In Vitro Toxicity of GCV for Kbalb-STK Cells

Colony Inhibition Time Course Assay

The Kbalb murine fibrosarcoma cell line was transduced with the STK vector and grown in standard tissue culture as described in Example 1 in order to select for a population of cells that all carry and express the STR vector. The Kbalb line is itself a transformed tumorigenic derivative of the BALB/3T3 clone A31 cell line (ATCC No CCL 163). STK vector stocks were obtained from the Y2 packaging line and used as described above. Fifty thousand cells were plated on 10 cm tissue culture dishes 18 hours prior to exposure to DXEE containing either 1 μM or 10 μM GCV for different periods of time. Medium was then removed, the plates were washed three times with sterile phosphate buffered saline to remove GCV and then fresh DMEM without GCV was added. Colonies were then counted 14 days later. The results shown in Table 3 demonstrated that the Kbalb-STK cell line was sensitive to killing by a brief exposure to GCV. The results were expressed as the number of colonies that grew on the GCV treated plates after 14 days in culture. The maximum number of colonies that could be counted was 150 per plate and plates with 150 or more colonies were scored as 150.

TABLE 2

| Kbalb-STK Colonies Counted | | |
|---|---|---|
| hours in GCV | 1 μm GCV | 10 μm GCV |
| 0 | 150 | 150 |
| 3 | 32 | 18 |
| 6 | 28 | 14 |
| 12 | 23 | 14 |
| 18 | 14 | 12 |
| 24 | 15 | 6 |
| 48 | 8 | 10 |

EXAMPLE 3

In Vitro Toxicity of GCV for Kbalb-STK and HCT-STK Human Colon Carcinoma Cells

Colony Inhibition Assay

Two cell lines were tested for their sensitivity to GCV. The HCT human colon carcinoma cell line was obtained from the ATCC (CCL 225) and transduced with the STK vector as in Example 1 to obtain the HCT-STK cell line. On day 0, $2 \times 10^3$ cells were plated on 60 mm plates using culture medium containing GCV at the levels indicated in Table 3. The plates were left for 10 to 14 days at 37° C. and then stained. The number of colonies were counted and the results are shown in Table 3. Plates containing a $\geq 150$ colonies were scored as 150. Cells expressing TK were sensitive to GCV and control cells containing no vector or the LNL vector were resistant.

TABLE 3

| cell line | GCV concentration (μM) | colonies |
|---|---|---|
| Kbalb | 0 | 150 |
| | 0.005 | 150 |
| | 0.05 | 150 |
| | 0.5 | 150 |
| | 5.0 | 150 |
| | 50 | 150 |
| Kbalb-LNL | 0 | 150 |
| | 0.005 | 150 |
| | 0.05 | 150 |
| | 0.5 | 150 |
| | 5.0 | 150 |
| | 50 | 150 |
| Kbalb-STK | 0 | 150 |
| | 0.005 | 150 |
| | 0.05 | 80 |
| | 0.5 | 12 |
| | 5.0 | 7 |
| | 50 | 6 |
| Kbalb-μTK | 0 | 150 |
| | 0.005 | 150 |
| | 0.05 | 48 |
| | 0.5 | 10 |
| | 5.0 | 9 |
| | 50 | 9 |
| HCT | 0 | 150 |
| | 0.005 | 150 |
| | 0.05 | 150 |
| | 0.5 | 150 |
| | 5.0 | 150 |
| | 50 | 150 |
| HCT-STK | 0 | 150 |
| | 0.005 | 150 |
| | 0.05 | 150 |

TABLE 3-continued

| cell line | GCV concentration (µM) | colonies |
|---|---|---|
| | 0.5 | 12 |
| | 5.0 | 1 |
| | 50 | 0 |

EXAMPLE 4
In Vivo Response to GCV Therapy Using Kbalb-STK and Kbalb-LNL Cells
Tumor Regression Assay Four groups of four BALB/c mice per group were injected subcutaneously (s.c.) with $2 \times 10^5$ cells in sterile saline per animal using the following cells or cell mixtures: Group 1, Kbalb-STK; Group 2, 90% Kbalb-STK and 10% Kbalb-LNL; Group 3, 50% each Kbalb-STK and Kbalb-LNL; Group 4, 100% Kbalb-LNL. Beginning three days after injection, GCV was administered interperitoneally (i.p.) twice daily at a dose of 150 mg GCV/kg mouse for 5 days. Tumor size at the injection site was determined from one animal from each group on days 0, 3, 9 and 17 from the time the cells were injected into the animals. The results shown in Table 4 indicate tumor growth occurred in all groups until day three. After initiation of GCV therapy, tumor size on day 9 remained the same as at day three and had regressed completely by day 17 in Groups 1, 2 and 3. Group 4 tumor growth continued unchecked throughout the duration of the experiment. These results clearly showed killing of both GCV sensitive and GCV resistant tumor cells in vivo in animals containing tumors consisting of cell mixtures.

TABLE 4

| Animal Group | day after injection | tumor diameter (mm) |
|---|---|---|
| 1 | 0 | 0 |
| | 3 | 2.5 |
| | 9 | 2.2 |
| | 17 | 0 |
| 2 | 0 | 0 |
| | 3 | 2.3 |
| | 9 | 2.3 |
| | 17 | 0 |
| 3 | 0 | 0 |
| | 3 | 2.4 |
| | 9 | 2.4 |
| | 17 | 0 |
| 4 | 0 | 0 |
| | 3 | 2.4 |
| | 9 | 8.0 |
| | 17 | 14.2 |

EXAMPLE 5
In Vivo Response to GCV Therapy Using Transduced Kbalb and EMT 6.8 Cell Populations
Host Survival and Targeting of Injected Kbalb-STK Cells to a Resident Kbalb-LNL or EMT 6.8 Tumor The EMT 6.8 murine mammary tumor cell line was obtained from the ATCC. Six groups of six BALB/c mice per group were injected i.p. on day 0 with $2 \times 10^5$ transduced tumor cells in sterile saline per animal as follows: Group 1, Kbalb-LNL; Group 2, Kbalb-STK; Group 3, 50% each Kbalb-STK and Kbalb-LNL. A fourth group, Group 4, of six BALB/c mice was injected i.p. on day 0 with $2 \times 10^5$ Kbalb-LNL cells and then 24 hours later with $1 \times 10^6$ Kbalb-STK cells injected i.p. On day five, 5 days after initial cell injections for all groups, daily GCV therapy (150 mg GCV/kg injected i.p. twice daily) was administered. Group 5 animals were injected i.p. with $2 \times 10^5$ EMT 6.8 cells on day 0 and followed over time. Group 6 animals were injected i.p. with $2 \times 10^5$ EMT 6.8 cells on day 0 and then injected with $1 \times 10^6$ Kbalb-STK cells on day 1 followed by GCV treatment (150 mg GCV/kg injected i.p. twice daily) starting on day 5. Survival of the animals was then followed over time. The results shown in Table 5 (number of animals surviving in each Group over time) demonstrated that a mixed population of tumor cells (Group 3) was killed in vivo by GVC therapy resulting in prolonged survival times compared to controls (Group 1). Five out of 6 Group 4 animals survived over the 30-day time period of the experiment. The result from Group 4 demonstrated that transduced tumor cells introduced into an area near a pre-existing tumor leads to regression of the pre-existing tumor after appropriate therapy is initiated. The results here also showed that peritoneal cavity tumors respond to the GCV therapy. These results also demonstrated that the daughter cells, which were injected into the subject animals after introduction of parental cancer cells into the peritoneal cavity, were able to migrate to or target the parental cells in vivo and killed them, which resulted in prolonged survival.

TABLE 5

| Animal Group | day after injection | number of surviving animals |
|---|---|---|
| 1 | 15 | 6 |
| | 16 | 4 |
| | 17 | 2 |
| | 1 | 80 |
| 2 | 15 | 6 |
| | 16 | 6 |
| | 17 | 6 |
| | 18 | 6 |
| | 19 | 6 |
| | 30 | 6 |
| 3 | 15 | 6 |
| | 16 | 6 |
| | 17 | 6 |
| | 18 | 6 |
| | 19 | 6 |
| | 30 | 6 |
| 4 | 15 | 6 |
| | 16 | 5 |
| | 17 | 5 |
| | 18 | 5 |
| | 19 | 5 |
| | 30 | 5 |
| 5 | 15 | 5 |
| | 16 | 5 |
| | 17 | 4 |
| | 30 | 0 |
| 6 | 15 | 5 |
| | 16 | 5 |
| | 17 | 5 |
| | 30 | 4 |

EXAMPLE 6
Demonstration of Preexisting Tumor Cell Killing in Vivo
Regression of Tumors that Preexisted in the Peritoneal Cavity for 1 to 5 days Prior to Introduction of Kbalb-STK Cells Six groups of mice were used to show the effect of Kbalb-STK cells on tumors that were derived from Kbalb-LNL cells previously injected into the peritoneum. Mice were injected i.p. as follows: Group 1 (control; 6 animals) $2 \times 10^5$ Kbalb-STK cells were injected on day 0 and given no further treatment; Group 2 (control; 4 animals) $2 \times 10^5$ Kbalb-LNL cells were injected on day 0 and given no further treatment; Group 3 (control; 10 animals) $2 \times 10^5$ Kbalb-LNL cells were injected on day 0 and given 150 mg GCV/kg i.p. b.i.d. for 2.5 days (total of 5 doses of GCV) starting 5 days after injection; Group 4 (8 animals) $2 \times 10^5$ Kbalb-LNL cells were injected on day 0 and then $1 \times 10^6$ Kbalb-STK cells were injected i.p. on day 5, followed by 150 mg GCV/kg i.p. b.i.d. for 2.5 days starting on day 9; Group 5 (8 animals) $2 \times 10^5$ Kbalb-LNL cells were injected on day 0 and then $1 \times 10^7$ Kbalb-STK cells were injected i.p. on day 5, followed by 150 mg GCV/kg i.p. b.i.d. for 2.5 days starting on day 9; Group 6 (12 animals) $2 \times 10^5$ Kbalb-LNL cells were injected on day 0 and then $1 \times 10^6$ Kbalb-STK cells were injected i.p. on day 1, followed by 150 mg GCV/kg i.p.b.i.d. for 2.5 days starting on day 5. No survivors in Groups 1, 2 or 3 were observed by 21 days after injection of cells, consistent with the course of tumor progression without any effective treatment. Group 6 animals had a mean survival of 31.6 days giving a p<0.0when compared to group 2 which had a mean survival of less than 19 days. Group 4 had a survival rate of 50% at 26 days and 25% at 43 days while Group 5 had a mean survival of 50% at 30 and 25% at 41 days after injection of Kbalb-LNL cells. The results demonstrated that a preexisting tumor was driven to regression by implantation of daughter cells and administration of GCV treatment.

EXAMPLE 7
In Vivo Response to GCV Therapy Using LNL 205 and 205-STK Cell Populations
Tumor Regression Assay Four groups of DBA/2 mice with 6 animals in each group were injected i.p. with $2 \times 10^5$ cells on day 0 and on day 1 (24 hours later) daily GCV therapy (150 mg GCV/kg, i.p. injection) was initiated and continued for the duration of the experiment. The 205 cell line is a methylcholanthrene-induced fibrosarcoma which was generated in DBA/2 mice. The 205 cell line was transduced by either the STK in the LNL vectors in accord with the procedures of Example 1 to yield 205-STK or LNL 205 cells. Tumor size from pairs of animals was measured at day 3, 9 and 15. Mice were injected as follows: Group 1, LNL $2 \times 10^5$ cells; Group 2, 50% each of LNL 205 and 205-STK cells; Group 3, 90% of LNL 205 (i.e. $1.8 \times 10^5$ cells) and 10% (i.e. $2 \times 10^4$ cells) of 205-STK cells; Group 4, 205-STK cells. Tumor regression occurred in all Group 2 and 4 animals by day 15 (no tumors detectable at day 15). Tumor regression occurred in 50% of Group 3 animals by day 15. Tumor growth in Group 1 occurred with all animals having tumors of at least 7 mm in diameter by day 15. These results showed that only a small proportion of the malignant cells in a subject need be genetically engineered with an appropriate gene to generate an acceptable daughter cell population for therapeutic efficacy.

EXAMPLE 8
Demonstration of an Immune Component in the Biological Response to Tumor Cells in Vivo
Immunization of Animals to a Second Challenge with Tumor Cells after Killing of Initial Tumor Cells by GCV Therapy Three groups of BALB/c mice were used as follows: Group 1, inject $2 \times 10^4$ Kbalb-STK cells s.c. (8 animals) with no further treatment; Group 2, (i) inject $2 \times 10^4$ Kbalb-STK cells s.c. and initiate GCV therapy (150 mg GCV/kg daily i.p.) 3 days post implant and continue for 5 days then (ii) inject $2 \times 10^4$ Kbalb cells s.q. 6 weeks after GCV therapy was discontinued (3 animals); Group 3, (i) inject $2 \times 10^4$ Kbalb-STK cells s.c. and initiate GCV therapy (150 mg GCV/kg daily i.p.) 3 days post implant and continue for 5 days then (ii) inject $2 \times 10^4$ Kbalb cells s.c. 8 weeks after GCV therapy was discontinued (3 animals). Tumor size in the animals was then determined 12 days after cell implantation. The average tumor size for the 8 Group 1 control animals that had tumors was 6.1 mm diameter. The Group 2 tumor sizes were 4.9, 0, 0 mm diameter (i.e. 2 of the animals had no detectable tumor). No tumor was detectable in any of the group 3 animals. These results show effective immunization related to initial tumor destruction in vivo. The immunization results are statistically significant using the T test for significance (P=<0.001). The experiment was repeated a second time using the 205 tumor cell line. On day 1, 28 mice were injected with a population consisting of $1 \times 10^6$ 205-STK (100%) or 205-STK (50%) and 205 (50%) cells and GCV treatment was initiated on the same day and continued for 5 days. On day 43, $1 \times 10^5$ 205 tumor cells were injected subcutaneously. 13 of the 28 mice had no detectable tumors at 12 days after challenge.

EXAMPLE 9
In Vivo Response to GCV Therapy Using a Human Neuroblastoma Cell Line
Tumor Inhibition Assay The human neuroblastoma cell line, SK-N-MC (ATCC No. HTB 10) was transduced with the STK vector and grown in medium containing G418 in order to generate the SKNMC-STK cell line. Three BALB/c mice were injected with $1.5 \times 10^6$ SKNMC-STK cells s.c. and, for two of the animals, GCV therapy (150 mg GCV/kg i.p. daily injection) was initiated the following day (day 1). The remaining animal was not treated with GCV. At day 6 tumor size was determined for each animal. The untreated control animal had a tumor at the site of injection 6.5 mm in diameter. No tumor was detected in either of the two animals that received GCV therapy. This result demonstrated that TK vectors currently available adequately express the TK gene in human tumor cells in vivo so that GCV therapy is effective. This experiment also demonstrated that human tumor cells are susceptible to killing by a subject in vivo. The observation that human cells respond to this therapeutic method, shows that cancers from other species (human) are amenable to treatment by the disclosed method.

EXAMPLE 10
Daughter Cells in a Mixture that Leads to Killing of Parental Cells
Tumor Inhibition Assay in an Intraderitoneal Model BALE/c mice were injected i.p. on day 0 with Kbalb, Kbalb-LNL or Kbalb-STK cell populations as described in Example 4 above. The animal groups were injected with cell populations that consisted of: Group 1 (5 animals; $2 \times 10^5$ cells; no GCV treatment) Kbalb-LNL cells; Group 2 (9 animals; $2 \times 10^5$ cells; 150 mg GCV/kg i.p., b.i.d.×2.5 days starting on day 5) Kbalb-LNL cells; Group 3 (3 animals; $2 \times 10^5$, cells; no GCV treatment) Kbalb-STK cells; Group 4 (12 animals; $2 \times 10^5$ cells; 150 mg GCV/kg i.p., b.i.d.×2.5 days starting on day 5) Kbalb-STK cells; Group 5 (12 animals; $2 \times 10^5$ cells; 150 mg GCV/kg i.p., b.i.d.×2.5 days starting on day 5) 50% Kbalb-STK and 50% Kbalb-LNL cells. All animals in Groups 1, 2 and 3 had a mean survival of less than 20 days and no animals survived longer than 21 days. Group 4 and 5 animals had a mean survival time longer than 30 days, with Group 5 having a 100% survival at 58 days. Group 4 animals had a survival rate of 83% at 80 days and Group 5 had a survival rate of 66% at 80 days. The Group 5 results demonstrated that daughter cells can be present in a tumor containing parental cells and still result in an effective antitumor response.

EXAMPLE 11
Daughter Cells Generated in Vivo by Transfer of the TX Gene into a Preexisting Tumor Tumor Inhibition Protocol Using Retroviral Vector Stock to Transfer the TK Gene into Kbalb Cells Balb/c mice were injected i.p. with $5 \times 10^4$ Kbalb tumor cells on day 0. On days 1, 2 and 3 the mice were injected i.p. with either LNL or STK stock (about 4.0 ml/injection; vector titer for either virus was about $1 \times 10^6$ cfu/ml) in DMEM with serum. Three groups of animals were followed. Group 1 received LNL vector and GCV therapy (150 mg/kg b.i.d.) for 2.5 days starting on day 5. Group 2 received STK vector and no GCV therapy. Group 3 received STK vector and GCV therapy for 2.5 days starting on day 5. There were no survivors in Group 2 by 18 days after injection of cells and no survivors after 26 days in Group 1. Survivors (25%) were observed in Group 3 at 35 days. The results demonstrated that GCV treatment resulted in prolonged survival after in vivo gene transfer into the tumor cells.

EXAMPLE 12
In Vivo Response to GCV Therapy Using a Human Ovarian Carcinoma Cell Line
Tumor Inhibition Assay in Vivo Two groups of Balb/c mice were injected i.p. One group was injected with $2 \times 10^5$ Kbalb-LNL cells on day 0 and then with $2 \times 10^6$ SKOV-STK cells i.p. on day 1 and then given no further treatment (Group 1; 4 animals). The other group was injected with $2 \times 10^5$ Kbalb-LNL cells on day 0 and then with $2 \times 10^6$ SKOV-STK cells i.p. on day 2, followed by 150 mg GCV/kg i.p. b.i.d. for 2.5 days (5 doses) starting on day 4 (Group 2; 4 animals). The SKOV-STK cell line was obtained by infection of the human ovarian adenocarcinoma cell line SK-OV-3 (obtained from the American Type Culture Collection—ATCC) with the STK vector as described above. Group 1 animals had a survival rate of 50% at 20 days and a survival rate of 0% at 25 days. Group 2 animals had a survival rate of 100% at 20 days and a survival rate of 75% at 25 days and at 55 days. The results demonstrated that, in this particularly preferred embodiment, a tumor carrier cell population derived from a cell line different from the parent tumor population and from a different species, could lead to killing of the parent tumor after GCV treatment. The result obtained using the human ovarian tumor cell line showed that cells derived from a tumor different from the parental cells could unexpectedly elicit a tumor killing response in vivo. By using human tumor cell lines in this Example, the clinical applicability of this method become apparent.

EXAMPLE 13
In Vitro Response to GCV Therapy Using a Mixture of Cell Lines
Killing of Cells Resistant to GCV in Vitro by GCV Sensitive Cells A cell mixing study was used to demonstrate killing of parental cells by daughter cells in tissue culture. Five different mixtures of Kbalb-STK and Kbalb-LNL cells were plated on 10 cm tissue culture plates and then treated with 10 µM GCV either at the time the cells were plated (Treatment 1) or when the cells reached confluence (Treatment 2; 3 trials) and then left for 14 days. After 14 days in GCV, the plates were stained and the number of colonies were counted. The cell mixtures consisted of the following: mixture 1, 100% Kbalb-LNL cells; mixture 2, 10% Kbalb-STK and 90% Kbalb-LNL cells; mixture 3, 50% Kbalb-STK and 50% Kbalb-LNL cells; mixture 4, 90% Kbalb-STK and 10% Kbalb-LNL cells, mixture 5, 100% Kbalb-STK cells. The results obtained are shown in Table 6 and give the number of colonies per 10 cm plate.

TABLE 6

| Cell mixture | Treatment 1: GCV added at time of plating | | Treatment 2: GCV added at cell confluence | |
| --- | --- | --- | --- | --- |
| 1 | TNTC* | TNTC | TNTC | TNTC |
| 2 | TNTC | 120 | 0 | 0 |
| 3 | TNTC | 4 | 0 | 0 |
| 4 | 95 | 0 | 0 | 0 |
| 5 | 8 | 0 | 0 | 0 |

*TNTC, too numerous to count (>150 colonies/plate).

The results showed that confluent cells were more efficiently killed than cells at a low plating density. The results obtained with mixture 2 shows that a relatively efficient mechanism for killing of parental cells exists when even a few daughter cells are in close proximity. Conditions in vivo would, on an approximation, mimic the Treatment 2 situation where cells are in close apposition with one another. Killing of Kbalb-LNL cells by GCV treatment of Kbalb-STK cells in tissue culture showed that a mechanism in addition to an immune response could be a component of the observed in vivo results showing killing of parental cells.

A similar experiment was conducted using Kbalb-LNL cells mixed with either HCT or HCT-STK as a source of lethally irradiated (3000 rads) tumor carrier cells. A total of $2 \times 10^6$ cells consisting of Kbalb-LNL and HCT or Kbalb-LNL and HCT-STK cells were plated on 10 cm plates. HCT cells were obtained from ATCC (CCL 225). GCV was added at the same time to the plates. The HCT and HCT-STK cells were irradiated prior to plating. Mixtures of 0, 101 50, 90 and 99% HCT with Kbalb-LNL gave plates with >150 colonies per plate. A similar series of mixtures of Kbalb-LNL and HCT-STK were plated in GCV. The 100% Kbalb-LNL population had >200 colonies per plate. The population consisting of 10% RCT-STK cells had 25 cells per plate and the 50% population had 4 colonies per plate. There were no colonies from populations consisting of 90% or 99% HCT-STK cells. Carrier cells that were lethally irradiated and expressing the TK gene thus mediated in vitro killing of GCV sensitive tumor cells.

EXAMPLE 14
In Vivo Response to GCV Therapy Using Lethally Irradiated Tumor Cells
Tumor Inhibition Assay in Vivo Two groups of 10 Balb/c mice were injected i.p. Group 1 was injected with $2 \times 10^5$ Kbalb-LNL cells on day 0 and then with $5 \times 10^6$ Kbalb-STK cells (lethally gamma irradiated with 3000 rads immediately prior to injection) i.p. on day 1 and again on day 2 and then given a course of GCV therapy (150 mg/kg i.p. b.i.d. for 2.5 days) starting on day three. Group 2 was injected with $2 \times 10^5$ Kbalb-LNL cells on day 0 and then with $5 \times 10^6$ Kbalb-LNL cells (lethally gamma irradiated with 3000 rads immediately prior to injection) i.p. on day 1 and again on day 2 and then given a course of GCV therapy (150 mg/kg i.p. b.i.d. for 2.5 days) starting on day three. The Group 2 controls that did not receive any Kbalb-STK cells had a survival rate of 20% at 20 days, 10% at 21 days and 0% at 24 days. The Group 1 animals had a survival rate of 100% at 25 days, 30% at 40 days, 10% at 43 days and 0% at 68 days. Treatment of lethally irradiated daughter cells with GCV in vivo led to the prolonged survival of animals carrying parental cells.

A tissue culture study was carried out to determine the toxicity of GCV toward lethally irradiated Kbalb-STK and Kbalb-LNL cells (3000 rads of gamma radiation). Cells were radiated, plated at subconfluence and then exposed to 10 μM GCV at different times after plating. In no case were any colonies observed to grow after radiation, showing that the 3000 rad dose was in fact lethal. Kbalb-LNL cells exposed to GCV at 0, 2, 4 and 6 days after plating remained attached to the plates in small numbers at 28 days after plating. The cells were alive but unable to divide. Kbalb-STK cells exposed to GCV at 0 days after plating (i.e. GCV added at the same time the cells were plated) were all killed by 7 days after plating. No cells were found that remained attached to the plate. Kbalb-STK cells exposed to GCV at 2, 4 and 6 days after plating remained attached to the plates at 14 days after plating, but none were observed attached to the plates at 28 days. This result showed that lethally radiated Kbalb-STK cells were sensitive to GCV killing, particularly when exposed to GCV immediately after irradiation. This result may be due to GCV toxicity associated with DNA synthesis and repair after irradiation of Kbalb-STK cells.

EXAMPLE 15

In Vitro Response to GCV Treatment Using Tumor Cells that Express the HSV TK Gene Mechanism of Cell Death in Vitro Kbalb and Kbalb-STK tumor cells were plated separately and exposed to GCV. The cells were examined morphologically at different times over a period of several days. Examination by light microscopy revealed that cell death of the Kbalb-STK cells occurred by a process of apoptosis. The Kbalb-STK cells were characterized by pronounced cell shrinkage, vesicle formation and nuclear chromatin condensation, all of which are indicative of apoptosis (Cotter et al., *Anticancer Res.*, 10, 1153, (1990)). Kbalb cells did not demonstrate any detectable morphological changes and were not killed by GCV. Further analysis demonstrated that dead and dying Kbalb-STK cells detached from the tissue culture plates and when tissue culture medium containing these cells in GCV were transferred to plates containing healthy Kbalb cells, most of the Kbalb cells died. Killing of Kbalb cells in the presence of cells dying by apoptosis that was induced by GCV shows that a toxic metabolite, possibly phosphorylated GCV, was responsible for toxicity toward Kbalb cells. Kbalb cells obtained the toxic GCV metabolite directly and/or indirectly from the Kbalb-STK cells, presumably by engulfing apoptotic bodies derived from the dead cells. This mechanism of cell killing occurs without the participation of any immune response because Kbalb cells do not mediate any known immune responses. Because tumor cell killing can occur in vivo without any GCV therapy (Example 8), multiple mechanisms of tumor cell killing occur in this system.

EXAMPLE 16

Projected Phase I Study Involving Administration of HSV-TK Modified Ovarian Tumor Cells I.P. with Subsequent Ganciclovir Therapy The maximum tolerated dose (MTD) (up to $1 \times 10^{10}$ cells per dose) of the genetically-modified tumor cells of Example 11 will be determined. Four patients will initially receive $3 \times 10^7$ HSV-TK positive, irradiated tumor cells I.P. on day 0. Approximately twenty-four hours after the I.P. infusion the patient will be started on a seven-day course of ganciclovir. Two weeks after the termination of ganciclovir therapy the patient will be reevaluated in terms of side effects from treatment and disease state. If no adverse toxicity occurred from the previous I.P. tumor injection and ganciclovir therapy and there appears to be no evidence of progressing tumor which would require chemotherapy, then the patient will be eligible for the next dose. This schedule will continue for doses of $1 \times 10^8$, $3 \times 10^8$ for Group 1. If no adverse side effects warranting the stoppage of therapy are reported in Group 1 then Group 2 patients will at one dose level higher, and this pattern will continue through the four groups. If a patient has to drop out of the study for reasons other than toxicity, then another patient may be added to the group and will begin therapy at the lowest dose for that group.

The patients will be admitted to the hospital for the first eight days of each cycle. The vaccine is given on day 1 and ganciclovir on days 2–8. The treatment is repeated at three-week intervals for a total of three cycles of treatment. At the completion of treatment, patients will be followed regularly until and if there is progression of disease.

Vaccine and Administration

Patients will be assigned in order of entrance on study to one of the four treatment schedules below. The dose escalates with each treatment unless any toxicity of Grade II or higher level has occurred. For Grade II toxicity (except for neutropenia or thrombocytopenia) the dose is repeated but physician discretion could lower the dose if overall toxicity is of concern. For Grade III or IV toxicity, the dose is lowered one level.

| Patients | First Dose | Second Dose | Third Dose |
| --- | --- | --- | --- |
| 1–4 | $3 \times 10^7$ | $1 \times 10^8$ | $3 \times 10^8$ |
| 5–8 | $1 \times 10^8$ | $3 \times 10^8$ | $1 \times 10^9$ |
| 9–12 | $3 \times 10^8$ | $1 \times 10^9$ | $3 \times 10^9$ |
| 13–16 | $1 \times 10^9$ | $3 \times 10^9$ | $1 \times 10^{10}$ |

The vaccine is prepared in 1000 cc of normal saline and administered through a small intraperitoneal catheter which is inserted on the day of treatment and removed after the 1-hour infusion. Catheter placement and diffusion of fluid will be checked by a technician flow study prior to the vaccine.

Ganciclovir is a nucleoside analog. It is an FDA-approved drug for the treatment of cytomegalovirus infection. It is excreted by the kidney and a creatinine clearance is a required pretreatment test. It is supplied as a sterile powder and is reconstituted with sterile water. For IV administration, it is prepared in 100 cc of normal saline, or 5% dextrose and water, and infused over one hour.

The standard dose of ganciclovir is 5 mg/kg b.i.d. when patients have a creatinine clearance >80. If the CrCL is 50–79, the dose is 2.5 mg/kg b.i.d. Daily CBC and platelet counts will be obtained during treatment. The drug should be stopped if the absolute granulocyte count falls below 750 or the platelets are less than 50,000.

EXAMPLE 17

In Vivo Killing of Rat Brain Tumors by a Combination of Cell Lines Expressing a Cytokine and the HSV-TK Gene A cell mixing study was used to demonstrate in vivo killing of rat glioma cells in rat brains. A rat glioma cell line termed C6 was used for the experiments. The C6 rat tumor cell line was obtained from the ATCC, catalogue #CCL107. $5 \times 10^4$ of the C6 cells were inoculated intracranially (frontal lobe), as follows: Group 1—C6 cells alone; Group 2—a 5% mixture ($4.75 \times 10^4$ C6+$2.5 \times 10^3$ C6-STK) of irradiated C6 glioma cells expressing the HSV-TK gene (C6-STK); Group 3—with a 50% mixture of irradiated kbalb-IL-1 ($5 \times 10^4$) cells which produce the IL-1 cytokine; Group 4—with both $4.0 \times 10^3$ C6-STK and $5 \times 10^4$ kbalb-IL-1. The IL-1 cDNA gene was obtained from the Beckman Company and subcloned into the pPBNC retroviral vector at the Bam HI restriction site. The pBNC vector contains an LTR promoted neomycin resistance gene and CMV promoter which was used to promote the IL-1 gene. The IL-1 vector was termed PIL and transfected into the PA317 packaging cell line. Viral stock was then used to transduce cell lines. All these above procedures were performed using standard methods. Each group contained 3 animals. Each group received ganciclovir therapy for 6 days (60 mg/kg twice a day) beginning immediately after tumor inoculation.

| Group | C6 glioma ($5 \times 10^4$) | kbalb-IL-1 ($5 \times 10^{4*}$) | C6-STK ($2.5 \times 10^{3**}$) | GCV | Tumor Formation |
|---|---|---|---|---|---|
| 1 | + | − | − | + | + |
| 2 | + | − | + | + | + |
| 3 | + | + | − | + | +/− |
| 4 | + | + | + | + | − |

*irradiated with 10,000 rads
**irradiated with 3,000 rads

Rats were sacrificed approximately three weeks post tumor inoculation and the brains were removed. Each brain was evaluated for C6 tumor growth. Groups 1, 2, and 3 demonstrated tumor formation at the site of tumor inoculation. The results of Group 2 indicate that a 5% mixture of HSV-TK positive and negative cells does not contain enough ESV-TK positive cells to eradicate the tumor. Group 4 animals showed tumor eradication which demonstrates the powerful effect of administering a combination of tumor cells expressing the HSV-TK and cytokine gene. Administration of IL-1 secreting cells alone had an effect on the tumor mass, which indicates that cytokine-secreting cells can demonstrate the "bystander effect" as seen with the HSV-TK gene.

All of the patents and publications cited herein are incorporated by reference herein. It is to be understood that the preceding examples may be varied within the scope and spirit of the present invention with regard to the disease states that may be ameliorated and with regard to the methods of gene transfer and gene vectors used. Because many embodiments of the present invention are possible within the scope thereof, it is to be construed that the present invention is not limited to the specific embodiments thereof except as defined in the appended claims.

What is claimed is:

1. A method for eliminating cancer cells from a mammal afflicted with a cancerous tumor comprising:
   (a) administering to the mammal at or adjacent to the cancerous tumor a first population of transduced cells comprising a nucleic acid encoding a cytokine operably linked to a promoter, wherein the cytokine is expressed by the first population of transduced cells, and a second population of transduced cancer cells comprising a human herpes virus thymidine kinase gene operably linked to a promoter wherein expression of the human herpes virus thymidine kinase gene increases the susceptibility of the transduced cancer cells to an antiviral nucleoside analog; and
   (b) administering to the mammal an amount of the nucleoside analog effective to kill a portion of the transduced cancer cells, wherein the killing of the transduced cancer cells results in tumor regression.

2. A method for causing tumor regression in a mammal afflicted with cancer comprising:
   (a) transducing a first population of cells in vitro with a first vector comprising a nucleic acid encoding a cytokine operably linked to a first promoter to yield a first population of transduced cells which express the cytokine;
   (b) transducing a second population of cancer cells in vitro with a second vector comprising a nucleic acid encoding a human herpes virus thymidine kinase gene operably linked to a second promoter to yield a second population of transduced cancer cells;
   (c) administering the first and second populations of cells to the mammal afflicted with cancer at or adjacent to the tumor; and
   (d) administering an antiviral nucleoside analog to the mammal in an amount that is effective to cause tumor regression in the mammal by killing both transduced cancer cells and cells of the tumor.

3. The method of claim 2 wherein the first vector and the second vector are each a viral vector.

4. The method of claim 3 wherein the viral vector is a retroviral vector.

5. The method of claim 1 or 2 wherein, prior to step (a), the second population of cancer cells is explanted from the mammal.

6. The method of claim 1 or 2 wherein the second population of cancer cells is from an in vitro cultured tumor cell line.

7. The method of claim 1 or 2 further comprising irradiating the second population of transduced cancer cells prior to administration of the cells to the mammal so that they are viable but are unable to replicate.

8. The method of claim 1 or 2 wherein the second population of transduced cancer cells are from a cancer cell explanted from a mammal other than the afflicted mammal.

9. The method of claim 1 wherein the mammal is a human.

10. The method of claim 9 wherein the tumor is derived from human cells selected from the group consisting of central nervous system cells, lung cells, breast cells, ovary cells, and liver cells.

11. The method of claim 1 wherein the tumor is selected form the group consisting of human melanoma, human ovarian cancer, human neuroblastoma, human squamous cell carcinoma, human fibrosarcoma, and human pancreatic cancer.

12. The method of claim 2 wherein the cancer is selected from the group consisting of human melanoma, human ovarian cancer, human neuroblastoma, human squamous cell carcinoma, human fibrosarcoma, and human pancreatic cancer.

13. The method of claim 2 wherein the mammal is a human.

14. The method of claim 13 wherein the cancer is derived from human cells selected from the group consisting of central nervous system cells, lung cells, breast cells, ovary cells, and liver cells.

15. The method of claim 1 or 2 wherein the cytokine is selected from the group consisting of IL-1, IL-2, IL4, IL-6, alpha interferon and gamma interferon.

16. The method of claim 15 wherein the cytokine is IL-1.

17. The method of claim 1 or 2 wherein the antiviral nucleoside analog is ganciclovir or acyclovir.

* * * * *

UNITED STATES PATENT AND TRADEMARK OFFICE
CERTIFICATE OF CORRECTION

PATENT NO.    : 6,110,458
DATED         : August 29, 2000
INVENTOR(S)   : Scott M. Freeman et al.

It is certified that error appears in the above-identified patent and that said Letters Patent is hereby corrected as shown below:

Title page,
Item [75], Inventors, insert -- , N.Y. -- after "Rochester"; delete "both of N.Y." and insert -- MT -- therefor; and delete "Los Angeles, Calif." and insert -- Nevada, MO -- therefor.
Item [56], References Cited, OTHER PUBLICATIONS, insert the following 10 citations:
-- Gutierrez, A.A., et al., "Gene Therapy for Cancer", The Lancet, Vol. 339, pp. 715-721, (March 21, 1992).
K. A. Whartenby, et al., "Gene therapy for the treatment of cancer", Pharmacology and Therapeutics, 66, 175-190, (1995).
K. A. Whartenby, et al., "The Biology of Cancer GeneTherapy", Laboratory Investigation, 72, 131-145, (1995).
K. N. Wills, et al., Can. Gene Ther., 2, 191, (1995).
K. M. Wilson, et al., Arch. Otolaryn., 122, 746, (1996).
James M. Wilson, et al., "Hepatocyte-Directed Gene Transfer In Vivo Leads to Transient Improvement of Hypercholesterolemia in Low Density Lipoprotein Receptor-deficient Rabbits", J. Biol. Chem., 267, 963-967, (1992).
J. K. Wu, et al., Neurosurg., 35, 1094, (1994).
George Y. Wu, et al., "Receptor-mediated Gene Delivery in Vivo", J. Biol. Chem., 266, 14338-14342, (1991).
H.F. Acevedo et al., Cancer, 76, 1467, (1995).
Martin Zenke, et al., "Receptor-mediated Endocytosis of Transferrin-polycation Conjugates: An Efficient Way to Introduce DNA into Hematopoietic Cells", Proc. Nat'l. Acad. Sci. USA, 87, 3655-3659, (1990). --
Delete "Suguya" and insert -- Sugaya -- therefor.
Delete "Thiberghien" and insert -- Tiberghien -- therefor.

Column 4,
Line 45, delete "insolation" and insert -- isolation --.

Column 8,
Line 20, delete "STX" and insert -- STK --.
Line 20, delete "$\mu$TS" and insert -- $\mu$TK --.
Lines 29 and 30, "TX" and insert -- TK --.

Column 9,
Line 32, delete "STX" and insert -- STK --.

Column 10,
Line 67, delete "WERI" and insert -- WEHI --.

UNITED STATES PATENT AND TRADEMARK OFFICE
CERTIFICATE OF CORRECTION

PATENT NO.   : 6,110,458
DATED        : August 29, 2000
INVENTOR(S)  : Scott M. Freeman et al.

It is certified that error appears in the above-identified patent and that said Letters Patent is hereby corrected as shown below:

Column 11,
Line 53, delete "STR" and insert -- STK --.
Line 59, delete "DXEE" and insert -- DMEM --.

Column 16,
Line 46, delete "Intraderitoneal" and insert -- Intraperitoneal --.

Column 17,
Line 2, "TX" and insert -- TK --.

Column 18,
Line 34, delete "101" and insert -- 10, --.
Line 39, delete "RCT-STK" and insert -- HCT-STK --.

Column 21,
Line 29, delete "ESV-TK" and insert -- HSV-TK --.

Column 22,
Line 43, delete "form" and insert -- from -- therefor.

Signed and Sealed this

Sixth Day of May, 2003

JAMES E. ROGAN
*Director of the United States Patent and Trademark Office*